US010478359B2

(12) United States Patent
Kostic et al.

(10) Patent No.: US 10,478,359 B2
(45) Date of Patent: Nov. 19, 2019

(54) PERSON SUPPORT APPARATUSES WITH ACCELERATION DETECTION

(71) Applicant: Stryker Corporation, Kalamazoo, MI (US)

(72) Inventors: Marko N. Kostic, Portage, MI (US); Jonathan Mark Greenbank, Plainwell, MI (US); Sujay Sukumaran, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 412 days.

(21) Appl. No.: 15/346,779

(22) Filed: Nov. 9, 2016

(65) Prior Publication Data

US 2017/0128296 A1 May 11, 2017

Related U.S. Application Data

(60) Provisional application No. 62/253,167, filed on Nov. 10, 2015.

(51) Int. Cl.
*A61G 7/05* (2006.01)
*A61B 5/11* (2006.01)
(Continued)

(52) U.S. Cl.
CPC .......... *A61G 7/0527* (2016.11); *A61B 5/1115* (2013.01); *A61B 5/1121* (2013.01);
(Continued)

(58) Field of Classification Search
CPC ..................................................... A61G 7/05
(Continued)

(56) References Cited

U.S. PATENT DOCUMENTS 7,389,552 B1   6/2008 Reed et al.
8,281,433 B2   10/2012 Riley et al.
(Continued)

FOREIGN PATENT DOCUMENTS

EP   2508128 A1   10/2012

OTHER PUBLICATIONS

PCT International Search Report completed Mar. 8, 2017 for Application No. EP 16 19 8050, a foreign counterpart to U.S. Appl. No. 15/346,779.

(Continued)

*Primary Examiner* — Fredrick C Conley
(74) *Attorney, Agent, or Firm* — Warner Norcross + Judd LLP

(57) ABSTRACT

A person support apparatus, such as a bed, stretcher, cot, recliner, or the like, includes a support surface adapted to support a person, a litter, an accelerometer positioned below the support surface, and a controller that processes signals from the accelerometer to detect the presence or absence of a person on the support surface. In some embodiments, the controller also receives signals from a plurality of force sensors and uses them in combination with the accelerometer outputs to determine if the person has exited the person support apparatus. The controller may also be adapted to use outputs from the accelerometer to detect an impact against the person support apparatus, compare a magnitude of the detected impact with a threshold, and, if the threshold is exceeded, to issue a warning indicating potential damage to one or more of the plurality of force sensors.

20 Claims, 6 Drawing Sheets

(51) Int. Cl.

| | | |
|---|---|---|
| *A61B 5/00* | (2006.01) | |
| *A61G 1/02* | (2006.01) | |
| *A61G 7/012* | (2006.01) | |
| *A61G 7/015* | (2006.01) | |
| *A61G 7/018* | (2006.01) | |
| *G08B 21/04* | (2006.01) | |
| *G08B 21/22* | (2006.01) | |
| *G16H 40/63* | (2018.01) | |

(52) U.S. Cl.
CPC .......... *A61B 5/6892* (2013.01); *A61B 5/7275* (2013.01); *A61G 1/02* (2013.01); *A61G 7/012* (2013.01); *A61G 7/015* (2013.01); *A61G 7/018* (2013.01); *A61G 7/0506* (2013.01); *A61G 7/0507* (2013.01); *G08B 21/043* (2013.01); *G08B 21/0461* (2013.01); *G08B 21/22* (2013.01); *G16H 40/63* (2018.01); *A61B 5/1116* (2013.01); *A61B 2562/0219* (2013.01); *A61B 2562/0252* (2013.01); *A61G 2203/20* (2013.01); *A61G 2203/32* (2013.01); *A61G 2203/40* (2013.01); *A61G 2203/44* (2013.01); *A61G 2203/70* (2013.01)

(58) Field of Classification Search
USPC ..................................................... 5/613–618
See application file for complete search history.

(56) References Cited

U.S. PATENT DOCUMENTS

| | | |
|---|---|---|
| 8,287,452 B2 | 10/2012 | Young et al. |
| 8,444,558 B2 | 5/2013 | Young et al. |
| 8,672,853 B2 | 3/2014 | Young |
| 8,984,685 B2 | 3/2015 | Robertson et al. |
| 2007/0157385 A1 | 7/2007 | Lemire et al. |
| 2008/0120784 A1 | 5/2008 | Warner et al. |
| 2010/0101022 A1* | 4/2010 | Riley .................. A61B 5/0816 5/600 |
| 2010/0170043 A1 | 7/2010 | Young et al. |
| 2011/0144455 A1 | 6/2011 | Young et al. |
| 2013/0174345 A1 | 7/2013 | Leu et al. |
| 2013/0267791 A1 | 10/2013 | Halperin et al. |
| 2015/0008710 A1 | 1/2015 | Young et al. |
| 2015/0029029 A1 | 1/2015 | Hopcroft et al. |
| 2016/0089283 A1 | 3/2016 | DeLuca et al. |
| 2016/0314672 A1* | 10/2016 | Wiggermann ..... G08B 21/0446 |

OTHER PUBLICATIONS

PCT International Written Opinion completed Mar. 8, 2017 for Application No. EP 16 19 8050, a foreign counterpart to U.S. Appl. No. 15/346,779.

* cited by examiner

PERSON SUPPORT APPARATUSES WITH ACCELERATION DETECTION

CROSS-REFERENCE TO RELATED APPLICATIONS

This application claims priority to U.S. provisional patent application Ser. No. 62/253,167 filed Nov. 10, 2015, by inventors Marko Kostic et al. and entitled PERSON SUPPORT APPARATUSES WITH ACCELERATION DETECTION, the complete disclosure of which is incorporated herein by reference.

BACKGROUND

The present disclosure relates to person support apparatuses, such as beds, cots, and the like, that may be used in medical facilities, long-term care facilities, and/or in home-care situations.

Person support apparatuses come in a variety of different forms, such as cots, beds, stretchers, recliners, and the like. Such person support apparatuses include a support surface adapted to support a person thereon. In some person support apparatuses, one or more sensors for sensing a weight of a person positioned on the support surface are provided. Some person support apparatuses also have one or more lifts for changing a height of the support surface. Still further, some person support apparatuses have an exit detection system that is adapted to issue an alert if the occupant of the person support apparatus exits, or is about to exit, the person support apparatus.

SUMMARY

According to various embodiments, a person support apparatus is disclosed herein that includes one or more accelerometers that are used for one or more of the following purposes: to detect and assess impacts of the person support apparatus; to provide enhanced functionality to an exit detection system, such as, but not limited to, automatic arming and re-arming of the exit detection system; to provide enhanced functionality to a scale system, such as, but not limited to, improved immunity to noise and other unwanted signals during the weighing process; to estimate a location and/or detect movement of an occupant of the person support apparatus, including exiting movement; and to estimate locations of disturbances or impacts on the person support apparatus. Still other features and functions according to other embodiments are described in greater detail below.

According to one embodiment, a person support apparatus is provided that includes a support surface, a litter, an accelerometer, and a controller. The support surface is adapted to support a cushioning structure and a person thereon, and includes a first section and a second section. The first section is pivotable between a raised orientation and a lowered orientation. The litter is adapted to support the support surface. The accelerometer is positioned below the cushioning structure and coupled to at least one of the support surface and the litter. The controller communicates with the accelerometer and is adapted to process signals from the accelerometer to detect a presence or absence of the person on the support surface.

According to another embodiment, a person support apparatus is provided that includes a support surface, a litter, first and second accelerometers, a memory, and a controller. The support surface is adapted to support a person thereon. The litter supports the support surface. The first and second accelerometers are coupled to at least one of the support surface and the litter. The memory contains information regarding the relative position of the first accelerometer with respect to the second accelerometer. The controller communicates with the first and second accelerometers and is adapted to use the information and signals from the first and second accelerometers in order to estimate a location of a disturbance to the person support apparatus.

According to another embodiment, a person support apparatus is provided that includes a support surface, a litter, a plurality of force sensors, an accelerometer, and a controller. The support surface is adapted to support a person thereon. The litter supports the support surface. The plurality of force sensors detect a load that includes the weight of the support surface and the person when the person is supported on the support surface. The accelerometer is coupled to at least one of the support surface and the litter. The controller communicates with the accelerometer and the plurality of force sensors and is adapted to determine if the person has exited the person support apparatus based upon a combination of signals from both the accelerometer and the plurality of force sensors.

According to still another embodiment, a person support apparatus is provided that includes a support surface, a litter, a lift subsystem, a height sensor, a plurality of force sensors, and a controller. The support surface is adapted to support a person thereon. The litter supports the support surface. The lift subsystem raises and lowers a height of the support surface. The height sensor measures changes in the height of the support surface. The plurality of force sensors detect a load that includes the weight of the support surface and the person when the person is supported on the support surface. The controller communicates with the height sensor and the plurality of force sensors and is adapted to determine an amount of weight exerted on the support surface based on outputs from the plurality of force sensors. The controller is further adapted to determine if a rollover hazard exists based upon the amount of weight exerted on the support surface and the height of the support surface.

According to still another embodiment, a person support apparatus is provided that includes a support surface, a litter, a plurality of force sensors, an accelerometer, and a controller. The support surface is adapted to support a person thereon. The litter supports the support surface. The plurality of force sensors detect a load that includes the weight of the support surface and the person when the person is supported on the support surface. The accelerometer is coupled to at least one of the support surface and the litter. The controller communicates with the accelerometer and the plurality of force sensors and is adapted to use outputs from the accelerometer to detect an impact against the person support apparatus. The controller is further adapted to compare a magnitude of the detected impact with a threshold, and, if the threshold is exceeded, to issue a warning indicating potential damage to one or more of the plurality of force sensors.

According to still another embodiment, a person support apparatus is provided that includes a support surface, a litter, an accelerometer, an exit detection system, and a controller. The support surface is adapted to support a cushioning structure and a person thereon. The support surface includes a first section and a second section wherein the first section is pivotable between a raised orientation and a lowered orientation. The litter supports the support surface. The accelerometer is positioned below the cushioning structure and coupled to at least one of the support surface and the litter. The exit detection system has an armed state in which the exit detection system issues an alert if the person exits the support surface, and a disarmed state in which the exit detection system does not issue an alert if the person exits the support surface. The controller communicates with the accelerometer and the exit detection system and is adapted to automatically switch the exit detection system to the armed state when the presence of the person on the support surface is detected.

In still another embodiment, a person support apparatus is provided that includes a support surface, a litter, an accelerometer, a plurality of force sensors, and a controller. The support surface is adapted to support a cushioning structure and a person thereon. The litter supports the support surface. The accelerometer is positioned below the cushioning structure and coupled to at least one of the support surface and the litter. The plurality of force sensors detect a load that includes the weight of the support surface and the person when the person is supported on the support surface. The controller communicates with the accelerometer and the plurality of force sensors and is adapted to use outputs from the accelerometer to filter a contemporaneous output from at least one of the plurality of force sensors.

According to still other embodiments, the one or more accelerometers are positioned below the support surface. In some such embodiments, the accelerometers are coupled to an underside of the support surface, while in other such embodiments, the accelerometers are fixedly coupled to the litter and do not move when one or more sections of the support surface pivot.

In some embodiments, the plurality of force sensors are load cells adapted to support the litter.

The controller, in at least one embodiment, is adapted to automatically execute a task in response to the presence of the person on the support surface. The task may include transmitting a message to a temperature controller positioned off-board of the person support apparatus; or it may include changing a state of a light adapted to provide illumination to the person; or it may include enabling a feature of the person support apparatus; or it may include changing a volume of an audio source; or it may include other actions.

In some embodiments, the controller is adapted to store in the memory a magnitude of any detected disturbances and times at which the disturbances occurred. A display may be included that displays the magnitude and time of the disturbance. In those embodiments where the controller compares a magnitude of the display to a threshold, the controller may also perform at least one of the following if the magnitude exceeds the threshold: (1) issue an alert; (2) disable an actuator on the person support apparatus; (3) transmit a message to a remote device; (4) forward outputs from the first and second accelerometers to another device; (5) issue a warning indicating potential damage to the plurality of force sensors; and (6) use outputs from the first and second accelerometers to filter a signal from a sensor other than the first and second accelerometers.

In some embodiments, the controller is adapted to automatically zero a weight reading and/or take a tare weight reading from the plurality of force sensors when the person is absent from the person support apparatus, as detected by the one or more accelerometers. When either of these actions is done, the controller sends a message, in some embodiments, to a user interface of the person support apparatus indicating that the weight reading has been automatically zeroed and/or that a new tare weight reading has been taken.

The controller, in some embodiments, uses the outputs from the plurality of force sensors to determine a center of gravity of the load applied to the support surface. In some embodiments, the controller uses this center of gravity when determining if a rollover hazard exists.

In still other embodiments, the controller measures the person's weight based upon outputs from the plurality of force sensors and determines if the measured weight is valid based upon outputs from the accelerometer.

The person support apparatus, in some embodiments, includes a user interface with a control that has a first setting and a second setting. The controller, when the control is in the first setting, automatically switches the exit detection system to the armed state when the presence of the person on the support surface is detected. The controller, when the control is in the second setting, does not automatically switch the exit detection system to the armed state when the presence of the person on the support surface is detected.

The controller is also adapted, in some embodiments, to distinguish between inanimate objects being placed on the support surface and the person entering the support surface based upon the signals from the accelerometer.

The controller may further be adapted to filter out recurring vibrations from a therapy device used in conjunction with treatment of the person such that the controller is able to determine an accurate weight of the person while the therapy device is creating vibrations. The therapy device may be a pump positioned on the person support apparatus, such as a pump used to treat or prevent deep vein thrombosis, or it may be another type of therapy device.

Before the various embodiments disclose herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
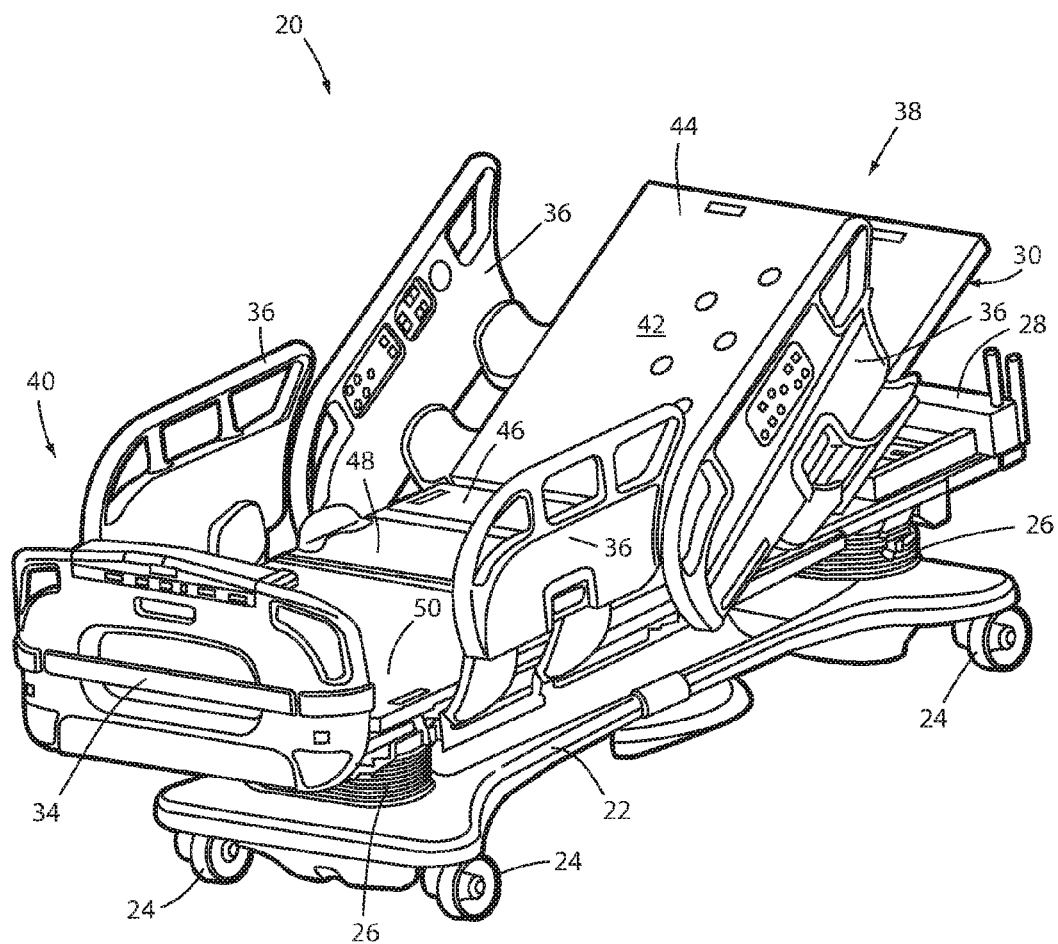
FIG. 1 is a perspective view of a person support apparatus into which one or more aspects of the present disclosure may be incorporated.

An illustrative person support apparatus 20 that incorporates one or more aspects of the present disclosure is shown in FIG. 1. Although the particular form of person support apparatus 20 illustrated in FIG. 1 is a bed adapted for use in a hospital or other medical setting, it will be understood that person support apparatus 20 could, in different embodiments, be a cot, a stretcher, a gurney, a recliner, an operating table, a residential bed, or any other structure capable of supporting a person, whether stationary or mobile and/or whether medical or residential.

In general, person support apparatus 20 includes a base 22 having a plurality of wheels 24, a pair of lifts 26 supported on the base, a litter frame 28 supported on the lifts 26, and a support deck 30 supported on the litter frame 28. Person support apparatus 20 further includes a headboard 32 (FIG. 5), a footboard 34, and a plurality of siderails 36. Siderails 36 are all shown in a raised position in FIG. 1 but are each individually movable to a lower position in which ingress into, and egress out of, person support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 38 and a foot end 40, each of whose height can be independently adjusted by the nearest lift 26. Person support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface 42 for a mattress (not shown in FIG. 1), or other soft cushion, so that a person may lie and/or sit thereon. Support deck 30 is made of a plurality of sections, some of which are pivotable about generally horizontal pivot axes. In the embodiment shown in FIG. 1, support deck 30 includes a head section 44, a seat section 46, a thigh section 48, and a foot section 50. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 48 and foot section 50 may also be pivotable about generally horizontal pivot axes.

Figure 2:
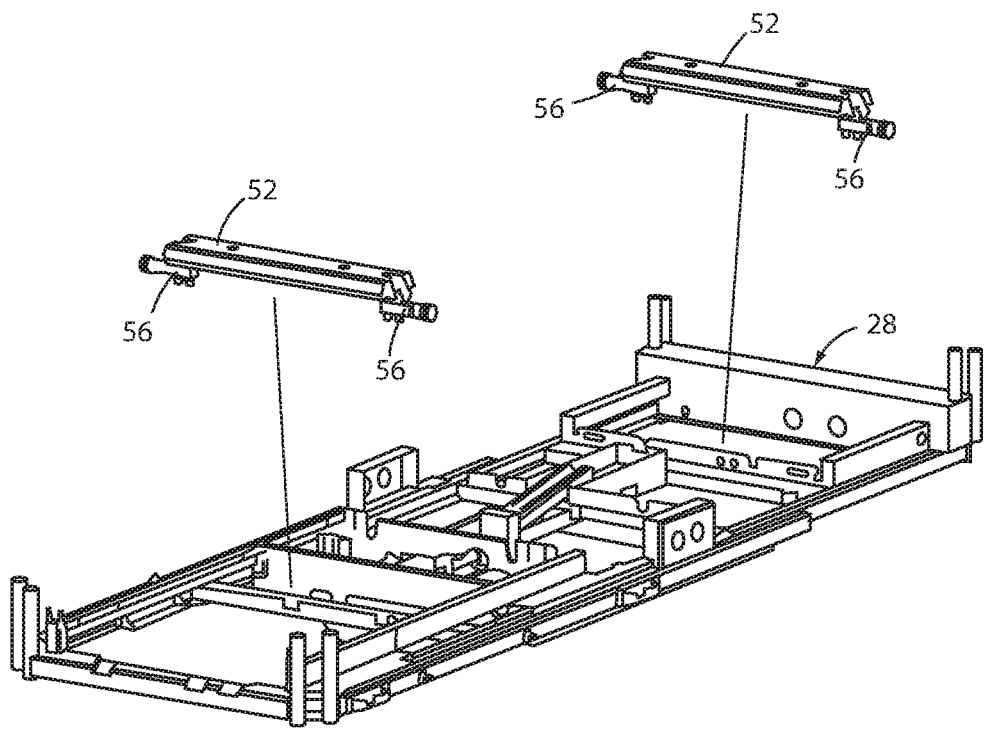
FIG. 2 is a perspective view of a litter frame of the person support apparatus of FIG. 1.

FIG. 2 illustrates in greater detail litter frame 28 separated from lifts 26 and base 22. Litter frame 28 is also shown in FIG. 2 with support deck 30 removed. Litter frame 28 is supported by two lift header assemblies 52. A first one of the lift header assemblies 52 is coupled to a top 54 (FIG. 3) of a first one of the lifts 26, and a second one of the lift header assemblies 52 is coupled to the top 54 of the second one of the lifts 26. Each lift header assembly 52 includes a pair of force sensors 56. The illustrated embodiment of person support apparatus 20 therefore includes a total of four force sensors 56, although it will be understood by those skilled in the art that different numbers of force sensors may be used in accordance with the principles of the present disclosure.

Force sensors 56 are configured to support litter frame 28 and detect downward forces exerted by an occupant of support deck 30. More specifically, force sensors 56 are configured such that they provide complete and exclusive mechanical support for litter frame 28 and all of the components that are supported on litter frame 28 (e.g. support deck 30, headboard 32, footboard 34, siderails 36, etc.). Because of this construction, force sensors 56 are adapted to detect the weight of not only those components of person support apparatus 20 that are supported by litter frame 28 (including litter frame 28 itself), but also any objects or persons who are wholly or partially being supported by support deck 30.

In at least one embodiment, force sensors 56 are conventional load cells. It will be understood by those skilled in the art, however, that force sensors 56 may be implemented as other types of sensors, such as, but not limited to, linear variable displacement transducers and/or any one or more capacitive, inductive, and/or resistive transducers that are configured to produce a changing output in response to changes in the force exerted against them.

Figure 3:
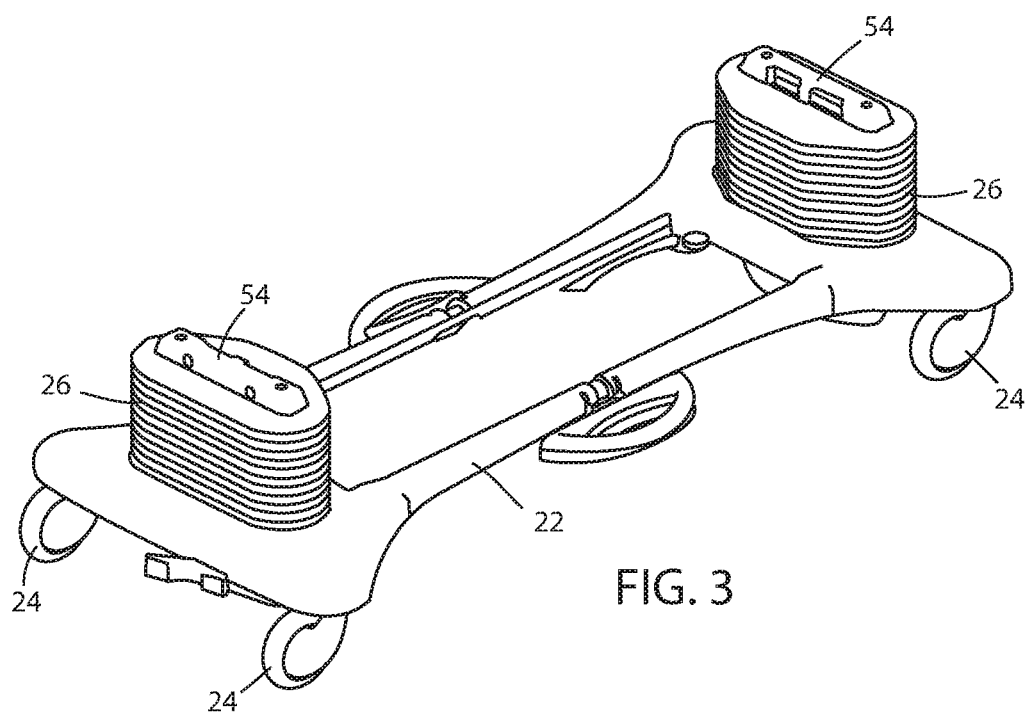
FIG. 3 is a perspective view of a base of the person support apparatus of FIG. 1.

As shown in FIGS. 1-3, the mechanical construction of person support apparatus 20 is the same as, or nearly the same as, the mechanical construction of the Model 3002 S3 bed manufactured and sold by Stryker Corporation of Kalamazoo, Mich. This mechanical construction is described in greater detail in the Stryker Maintenance Manual for the MedSurg Bed, Model 3002 S3, published in 2010 by Stryker Corporation of Kalamazoo, Mich., the complete disclosure of which is incorporated herein by reference. It will be understood by those skilled in the art that person support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of person support apparatus 20 may also take on forms different from what is disclosed in the aforementioned references.

Figure 4:
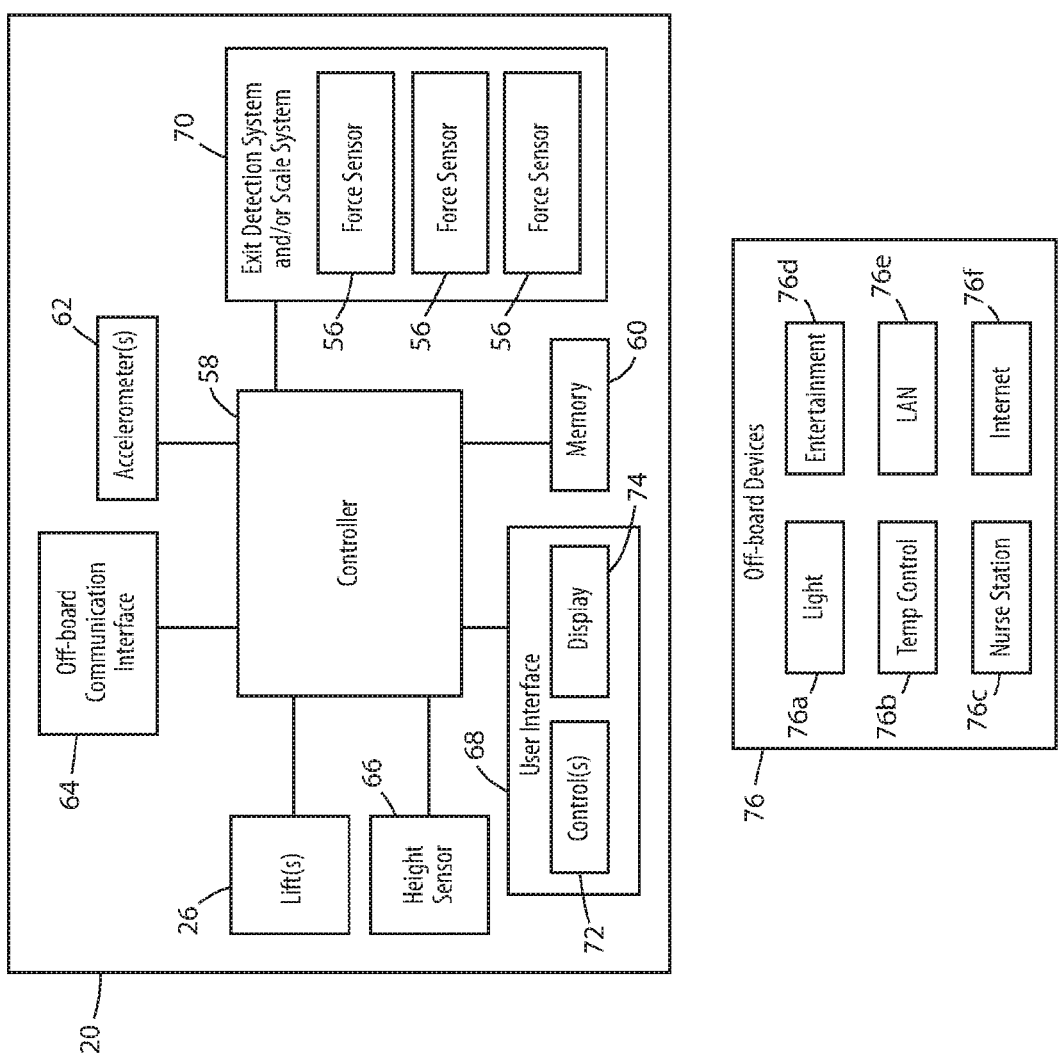
FIG. 4 is a diagram of various internal components of the person support apparatus of FIG. 1, including a plurality of off-board devices with which the person support apparatus may communicate, depending upon the particular embodiment of the person support apparatus.

As shown more clearly in FIG. 4, person support apparatus 20 also includes a controller 58, a memory 60, one or more accelerometers 62, an off-board communication interface 64, a height sensor 66, a user interface 68, and an exit detection system and/or scale system 70. User interface 68, in turn, includes at least one control 72 and, in some embodiments, a display 74, such as, but not limited to, a Liquid Crystal Display (LCD). System 70, which may be an exit detection system or a scale system or a combined exit detection and scale system, includes force sensors 56. Although FIG. 4 illustrates system 70 as having three force sensors 56, it will be understood that different numbers of sensors 56 may be used within system 70.

Controller 58 is constructed of any electrical component, or group of electrical components, that are capable of carrying out the functions described herein. In many embodiments, controller 58 is a conventional microcontroller, although not all such embodiments need include a microcontroller. In general, controller 58 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 58 in carrying out the functions described herein, as well as the data necessary for carrying out these functions, are stored in internal memory or external memory 60.

Height sensor 66 detects either an absolute or relative height of litter frame 28. More specifically, in one embodiment, height sensor 66 detects how far each lift 26 has extended from its lowest position. In another embodiment, height sensor 66 detects how high one or more points on litter frame 28 (or any component of person support apparatus 20 non-movably coupled to litter frame 28) is with respect to a reference (e.g. a floor, base 22, etc.). Height sensor reports its height readings to controller 58 which, as will be discussed in greater detail below, uses these readings and other information to determine if a potential rollover hazard exists for person support apparatus 20, at least in one embodiment of person support apparatus 20.

Off-board communication interface 64 is adapted to oversee communications between person support apparatus 20 and one or more off-board devices 76 that are located off-board of person support apparatus 20. In at least one embodiment, off-board communication interface 64 includes a WiFi transceiver (e.g. any of the IEEE 802.11 standards) that wirelessly communicates with one or more access points of a healthcare facility Local Area Network (LAN) 76e using the WiFi protocols. The LAN 76e, in at least one embodiment, is in communication with the Internet 76f, and therefore allows person support apparatus 20 to communicate with the Internet 76f. Off-board communication interface 64 may also include, either in addition to or in lieu of a WiFi transceiver, one or more other types of communication transceivers. Examples of these includes a standard nurse call cable that couples the person support apparatus to a conventional nurse call system via a cable, a ZigBee transceiver, a Bluetooth transceiver, and/or other types of transceivers. As will be discussed in greater detail below, off-board communication interface 64 enables controller 58 to communicate with still other types of off-board devices 76, such as one or more room lights 76a, one or more temperature controls (e.g. air conditioning, heat, etc.) for controlling the ambient temperature around person support apparatus 20, a nurses' station 76c, one or more entertainment devices 76d (e.g. a television or radio), and/or still other types of off-board devices.

User interface 68, as will be discussed in greater detail below, includes one or more controls 72 that enable a caregiver, or other user, to control various aspects of person support apparatus 20. User interface 68 is implemented in the embodiment shown in FIG. 1 as a control panel having a lid (flipped down in FIG. 1) underneath which is positioned a plurality of controls 72. The controls 72—which may be buttons, dials, switches, or other devices—allows a user to control various aspects of person support apparatus 20, including, but not limited to, exit detection system and/or scale system 70. User interface 68 also includes display 74 for displaying information regarding system 70, the status of person support apparatus 20, and other information which is discussed in greater detail below. Although FIG. 1 illustrates user interface 68 mounted to footboard 34, it will be understood that user interface 68 can be positioned elsewhere, and/or that one or more additional user interfaces can be added to person support apparatus 20 in different locations, such as the siderails 36, for controlling various aspects of person support apparatus 20.

System 70 which, as noted, may be an exit detection system, a scale system, or a combination of both an exit detection system and scale system, is adapted to process the outputs from forces sensors 56 to determine one or both of the following: (1) the weight of the occupant; and (2) when an occupant, such as, but not limited to, a patient, of person support apparatus 20 is likely to exit person support apparatus 20. With respect to the former function, controller 58 sums the outputs from each of the force sensors 56 to determine a total weight sensed by the force sensors 56, and then subtracts a known tare weight from this total weight value in order to determine the occupant's weight. With respect to the latter function, system 70 is adapted to determine when an occupant is likely to leave prior to the occupant actually leaving, and to issue an alert and/or notification to appropriate personnel so that proper steps can be taken in response to the occupant's imminent departure in a timely fashion. When performing this exit detection function, the particular structural details of system 70 can vary.

In one particular embodiment, system 70 is adapted to determine the center of gravity of whatever load is applied to force sensors 56. In other words, system 70 determines the center of gravity of the combined weight of an occupant, mattress, and/or any objects that are positioned on support deck 30 or litter frame 28, as well as those components of person support apparatus 20 whose weight is supported by force sensors 56 (e.g. litter frame 28, support deck 30, siderails 36, etc.). One manner of determining this center of gravity is disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. In other embodiments, other structures and/or algorithms may be used.

In at least one embodiment, person support apparatus 20 includes two accelerometers 62 that are physically coupled to litter 28 and longitudinally spaced apart from each such that one of the accelerometers is positioned generally near head end 38 and the other is positioned generally near foot end 40. The longitudinal distance S (see FIG. 5) between each accelerometer is stored in memory 60. In this embodiment, accelerometers 62 are positioned underneath support deck 30 but not coupled thereto. Instead, they are coupled to litter frame 28. Thus, when head end 38 of support deck 30 pivots upwardly about its generally horizontal axis, neither of the accelerometers 62 is pivoted. The same is true for any other pivoting movement of any of the other sections (e.g. 46, 48, and/or 50) of support deck 30. However, when litter frame 28 is raised or lowered via the action of lifts 26, both accelerometers 62 are raised or lowered along with litter frame 28. Accelerometers 62 are coupled to controller 58 and report their respective acceleration readings to controller 58.

Figure 5:
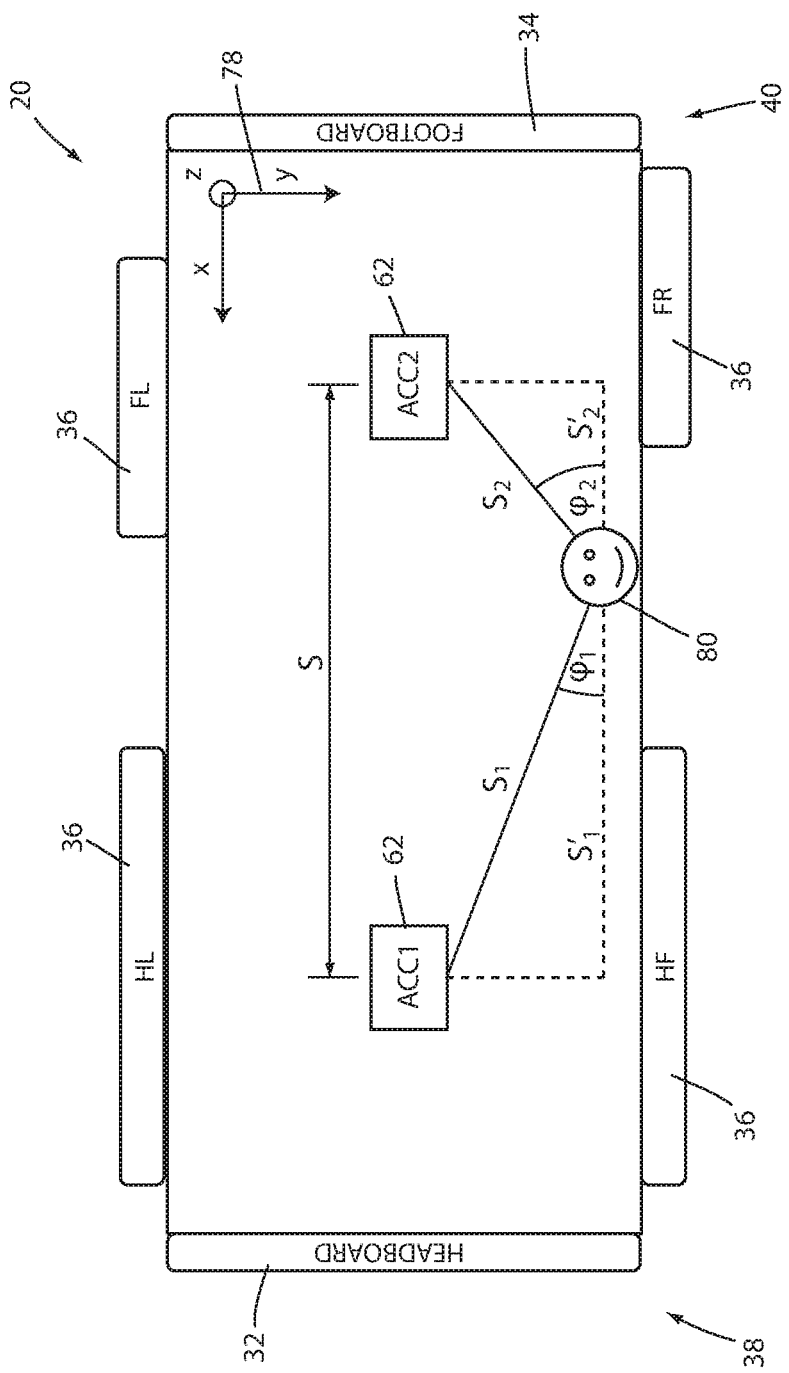
FIG. 5 is a plan view diagram of the person support apparatus of FIG. 1 illustrating the position of a pair of accelerometers.

In the embodiments discussed herein, each accelerometer 62 is a three-axis accelerometer adapted to detect accelerations in three orthogonal directions. As shown in FIG. 5, a coordinate frame of reference 78 is defined having an X-axis that runs from head end 38 to foot end 40, a Y-axis that extends from one side of person support apparatus 20 to its opposite side, and a Z-axis that extends substantially vertically. Accelerometers 62 detect accelerations along each of these X, Y, and Z axes. In some embodiments, the location of each accelerometer on person support apparatus 20 is determined within coordinate frame of reference 78 and stored in memory 60. In this manner, the outputs from accelerometers 62 due to impacts against person support apparatus 20 can be used to estimate a location on person support apparatus 20 where the impacts occurred.

The outputs of accelerometers 62 are used by controller 58 in various embodiments to perform one or more of the following functions: (1) detect the presence or absence of a person on support deck 30; (2) estimate a location of a disturbance or impact against person support apparatus 20; (3) detect movement of the occupant, such as, but not limited to, movement that may be indicative of the person intending to soon exit from person support apparatus 20 (e.g. sitting up and/or moving toward an side of support deck 30); (4) quantifying a magnitude of an impact against person support apparatus 20 and determining if any one or more components of person support apparatus 20 may have been detrimentally affected by the impact; (5) automatically re-arming the exit detection function of system 70 after the occupant has left and subsequently returned to person support apparatus 20; (6) filtering noise, artifacts, and other extraneous components out of the force signals from force sensors 56; and (7) automatically zeroing a scale system, such as may be contained within system 70.

Controller 58 uses the outputs of accelerometers 62 to detect the absence or presence of a person on support deck 30 by monitoring the occurrence, or lack of occurrence, of movement associated with a person while positioned on support deck 30. That is, when a person is occupying support deck 30, he or she will typically not lie perfectly still for extended periods of time. Instead, he or she will shift positions, move his or her arms or legs, roll over, turn, sit up or down, and make other motions while on support deck 30. These motions will cause corresponding motions and/or forces to be applied to support deck 30. Because support deck 30 is mechanically coupled to litter frame 28, the motions and/or accelerations experienced by support deck 30 due to patient movement will be transferred to litter frame 28. Accelerometers 62, which are coupled to litter frame 28 in at least one embodiment, detect the accelerations resulting from the movement of support deck 30 and the forces applied thereto.

Controller 58 compares the outputs of accelerometers 62 with one or more thresholds stored in memory 60 to determine whether a person is present or not on support deck 30. The thresholds includes at least one value for a magnitude of acceleration sensed in at least one direction. The thresholds also include one or more time values. Thus, for example, if controller 58 does not receive any acceleration signals from accelerometers 62 having magnitude greater than A (a first threshold) over a period of B (a time threshold), then controller 58 concludes that no person is present on support deck 30. On the other hand, if accelerometers 62 do detect one or more accelerations exceeding A over that same time period, controller 58 concludes that a person is present on support deck 30. In this example, a single magnitude threshold (A) has been used. It will be understood, however, that multiple different magnitude thresholds may be used. Thus, for example, a different threshold may be used for each of the different directions (X, Y, and Z) of coordinate frame of reference 78 in which acceleration is detectable by accelerometers 62. Also, different magnitude thresholds may be used for each of the individual accelerometers 62 such that a first one has a first set of thresholds, a second one has a second set of thresholds, and so on. The time thresholds may also vary according to the direction of the sensed accelerations (X, Y, and Z of frame of reference 78) and/or the particular accelerometer 62 that is detecting the accelerations.

In some embodiments, controller 58 is adapted to detect one or more vital signs of an occupant of person support apparatus 20 using accelerometers 62. Such vital signs include the occupant's breathing rate and/or heartrate. Both the pumping of the occupant's heart and his or her breathing create accelerations that are mechanically transferred to support deck 30, litter frame 28, and accelerometers 62. Exemplary methods for converting the vibrations caused by an occupant's breathing and/or heartbeat are disclosed in commonly assigned U.S. Pat. No. 7,699,784 issued to Wan Fong et al. and entitled SYSTEM FOR DETECTING AND MONITORING VITAL SIGNS, the complete disclosure of which is hereby incorporated herein by reference. Although the '784 patent discloses the use of load cells for detecting the patient's heart rate and/or breathing rate, it will be understood that the same or similar techniques for processing the outputs of the load cells disclosed therein can be applied to the accelerometers 62 disclosed herein.

When controller 58 is programmed to determine an occupant's vital signs using the outputs from accelerometers 62, controller 58 uses, in at least one embodiment, the absence or presence of such vital signs in making the determination of whether or not support deck 30 is occupied by a person or not. That is, in at least one embodiment, controller 58 combines the presence or absence of detected vital signs with the presence or absence of occupant motion to determine whether support deck 30 is occupied or not. In one such embodiment, controller 58 is programmed to conclude the following: (1) that support deck 30 is occupied whenever it detects a vital sign, regardless of the presence or absence of other movement (e.g. movement over the course of a threshold amount of time that results in accelerations exceeding one or more magnitude thresholds, as discussed above); (2) that support deck 30 is not occupied when no vital signs are detected and no other movement exceeding the aforementioned thresholds is detected; and (3) that support deck 30 is occupied if either vital signs are detected or movement exceeding the aforementioned thresholds is detected. Variations in this manner combining the movement and vital sign data to determine occupancy or vacancy can, of course, be made. As but one example, the presence or absence of detected vital signs can cause controller 58 to utilize different movement thresholds when deciding the occupancy status of support deck 30. Still other variations are possible.

In at least one other embodiment, controller 58 is programmed to determine the occupancy status of support deck 30 by also taking into account the outputs from force sensors 56. Thus, in some embodiments, controller 58 utilizes the movement and vital sign information from accelerometers 62 in combination with the force data from force sensors 56 to determine the occupancy status of support deck 30. In other embodiments, controller 58 uses a subset of these three pieces of data (vital signs, movement, and forces).

In those embodiments where controller 58 utilizes the outputs from force sensors 56 in determining the occupancy status of support deck 30, controller 58 is programmed, in at least one embodiment, to never conclude that person support apparatus 20 is occupied unless force sensors 56 detect a total weight that exceeds a minimum weight threshold. Such a minimum weight threshold may be based upon the smallest expected weight that a person utilizing person support apparatus 20 will have. When force sensors 56 detect a total weight that exceeds this minimum threshold, controller 58 is programmed to utilize any detectable indications of vital signs and/or occupant movement to determine the occupancy status of support deck 30, such as in the manners described above.

In at least one embodiment, controller 58 is programmed to utilize the outputs from force sensors 56 and accelerometers 62 to determine when an inanimate object is placed on support deck 30 or litter 28. In this embodiment, controller 58 detects the addition of a weight to support deck 30 via force sensors 56. If, after this weight addition is detected, controller 58 does not receive either vital sign or patient movement indications from accelerometers 62, controller 58 concludes that an inanimate object has been added to support deck 30 (or litter frame 28). Conversely, if controller 58 detects the removal of weight from support deck 30 via force sensors 56, but continues to receive acceleration signals from accelerometers 62 that are indicative of vital signs or occupant movement, controller 58 concludes that an inanimate object has been removed from support deck 30 (or litter frame 28).

Regardless of the particular data that controller 58 is programmed to utilize when determining the occupancy status of support deck 30, controller 58 is further programmed to time stamp and record in memory 60 the presence or absence of the occupant, as well as to make this information available for display on display 74. In addition, in at least one embodiment, controller 58 is programmed to transmit a message via off-board communication interface 64 to at least one off-board device 76 indicating that the occupant is present or absent, as the case may be. For example, in at least one embodiment, controller 58 is programmed to transmit a message to an off-board device 76 whenever an occupant is determined to have departed and whenever an occupant is determined to have returned. Once such off-board device this information is transmitted to is a computer that is part of the healthcare facility's local area network 76e. Such a computer may be in communication with one or more caregiver communication devices (e.g. badges, pagers, cell phones, or mobile computers) and may, depending upon user configurable settings, forward the occupancy status change information to the caregivers who are assigned to the occupant of person support apparatus 20.

In at least one embodiment, controller 58 is further programmed to automatically perform one or more tasks in response to an occupancy status change of support deck 30. One such task is the transmission of a command to one of the off-board devices 76. For example, in one embodiment, controller 58 is programmed to automatically transmit a command to an entertainment device 76d, such as a television, to turn down its volume and/or to turn itself off whenever an occupant is detected as having left person support apparatus 20. In such an embodiment, controller 58 is further programmed to automatically transmit an opposite command whenever the occupant is detected as having returned to person support apparatus 20 (e.g. turn the volume back up on the television or turn the television back on).

In another embodiment, controller 58 is programmed to transmit commands to automatically turn on light 76a whenever the presence of an occupant on support deck 30 is detected, and to turn off light 76a whenever the absence of the occupant on support deck 30 is detected. In still other embodiments, controller 58 is programmed to transmit commands to temperature control 76b (e.g. a thermostat) based upon the occupancy status of support deck 30. In one of these embodiments, controller 58 transmits an off command to the temperature control 76b when the occupant departs and an on command when the occupant returns. This reduces energy consumption while the occupant is away from person support apparatus 20.

In addition to, or in lieu of, commands sent to one or more off-board devices 76, controller 58 is programmed, in some embodiments, to execute one or more on-board tasks in response a change in the occupancy status of support deck 30. For example, in one such embodiment, controller 58 is programmed to enable and disable selected controls on person support apparatus 20 in response to an occupancy status change. The particular controls that are automatically enabled or disabled in response to occupancy changes can vary from embodiment to embodiment. In one such embodiment, controller 58 automatically re-arms system 70, when it is implemented as an exit detection system, when controller 58 determines that the person has re-occupied support deck 30. The automatic rearming of exit detection system 70 occurs when a control 72 on user interface is first manipulated to a first setting that turns on the auto-rearming function. This automatic rearming can be disabled by a user by manipulating the control to a second setting that turns off the auto-rearming function. Alternatively, the auto-rearming function is automatically turned on, in at least one embodiment, whenever exit detection system 70 is manually armed. In this alternative embodiment, exit detection system 70 must first be manually armed, but then automatically rearms itself anytime the person is detected as having returned to support deck 30. Still other variations of the automatic rearming of exit detection system 70 can be implemented.

The particular tasks that controller 58 automatically performs in response to a detected change in the occupancy status of support deck 30 are user-configurable. In order to instruct controller 58 to automatically perform one or more tasks in response to an occupancy change, a user selects a desired configuration utilizing user interface 68 and/or an off-board device 76 that is in communication with person support apparatus 20, such as one or more computers and/or servers that are in communication with LAN 76e. In this manner, for example, if a user wishes to only have exit detection system 70 rearm itself in response to a person returning to support deck 30, the user activates only the auto-rearming feature via one or more of the controls 72 on user interface 68. Alternatively, if the user wishes only to have a light turned on or off in response to an occupancy change, the user activates only the light control feature using the controls 72 of user interface 68. Utilizing the controls of user interface 68, the user is thereby able to select any individual task, or combination of tasks, that controller 58 will undertake in response to an occupancy change.

Controller 58 is also programmed, in at least one embodiment, to utilize the outputs of accelerometers 62 to estimate the location of a disturbance on person support apparatus 20, or the location of an impact of person support apparatus 20 with another object. Controller 58 performs this estimation by comparing the magnitudes of the accelerations detected by each of the accelerometers 62. If only two accelerometers are used, such as the embodiment shown in FIG. 5, controller 58 estimates where an impact has occurred along the X-direction of frame of reference 78, but does not estimate where the impact occurred along the Y direction of frame of reference 78. Controller 58 performs this estimate by using the known distance in the X-direction (labeled S in FIG. 5)

between accelerometers 62 and computing the ratio between the accelerations sensed by accelerometers in the X-direction.

Thus, for example, if the first accelerometer 62 (ACC 1 in FIG. 5) experiences an acceleration of $x_1$ and the second accelerometer 62 (ACC2 in FIG. 5) experiences an acceleration of $x_2$, controller 58 determines the values of $S'_1$ and $S'_2$ by using the following two equations: $(x_1/x_2)=(S'_1/S'_2)$ and $S'_1+S'_2=S$. The value $S'_1$ represents the distance from first accelerometer in the X direction to the point of impact (e.g. point 80 in FIG. 5) and the value $S'_2$ represents the distance from the second accelerometer in the X direction to the point of impact 80. Thus, an estimate of where along the X-axis the point of impact 80 is located can be computed by controller 58.

In at least one embodiment, controller 58 also uses the ratios of the sensed accelerations of the first and second accelerometers in FIG. 5 in the Z-direction to determine where along the X-axis the point of impact 80 is located. This is accomplished in a similar manner. That is, controller 58 is able to determine a second estimate of the values of $S'_1$ and $S'_2$ by using the following two equations: $(z_1/z_2)=(S'_1/S'_2)$ and $S'_1+S'_2=S$, where the values $z_1$ and $z_2$ refer to the accelerations sensed by the first and second accelerometers in the Z-direction, respectively. This second estimate of the location of the impact can be averaged with the estimate generated using the X-axis accelerometer readings, or combined in other ways, in order to provide a more accurate estimate of the impact location.

In other embodiments, a third accelerometer 62 is added to person support apparatus and placed at a location that is offset from the two accelerometers of FIG. 5 in the Y direction. Using equations similar to that described above, along with the known offset of the third accelerometer from one or both of the other two accelerometers in the Y direction, an estimate of the location of the impact in the Y direction can also be calculated by controller 58.

Figure 6:
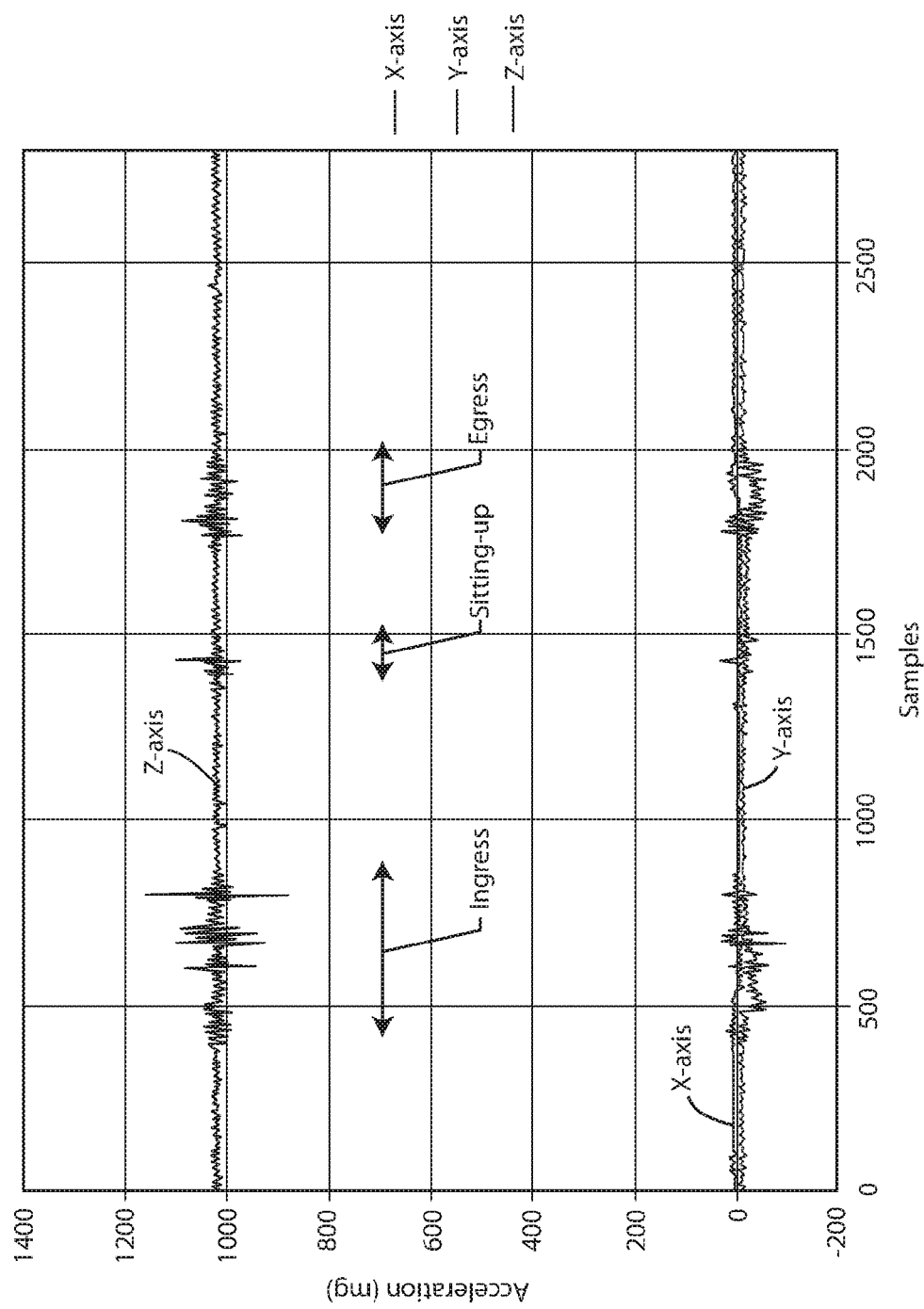
FIG. 6 is a graph of the outputs of one of the accelerometers of FIG. 5 taken while a first person entered the support surface, sat up on the support surface, and subsequently exited the support surface.
Figure 7:
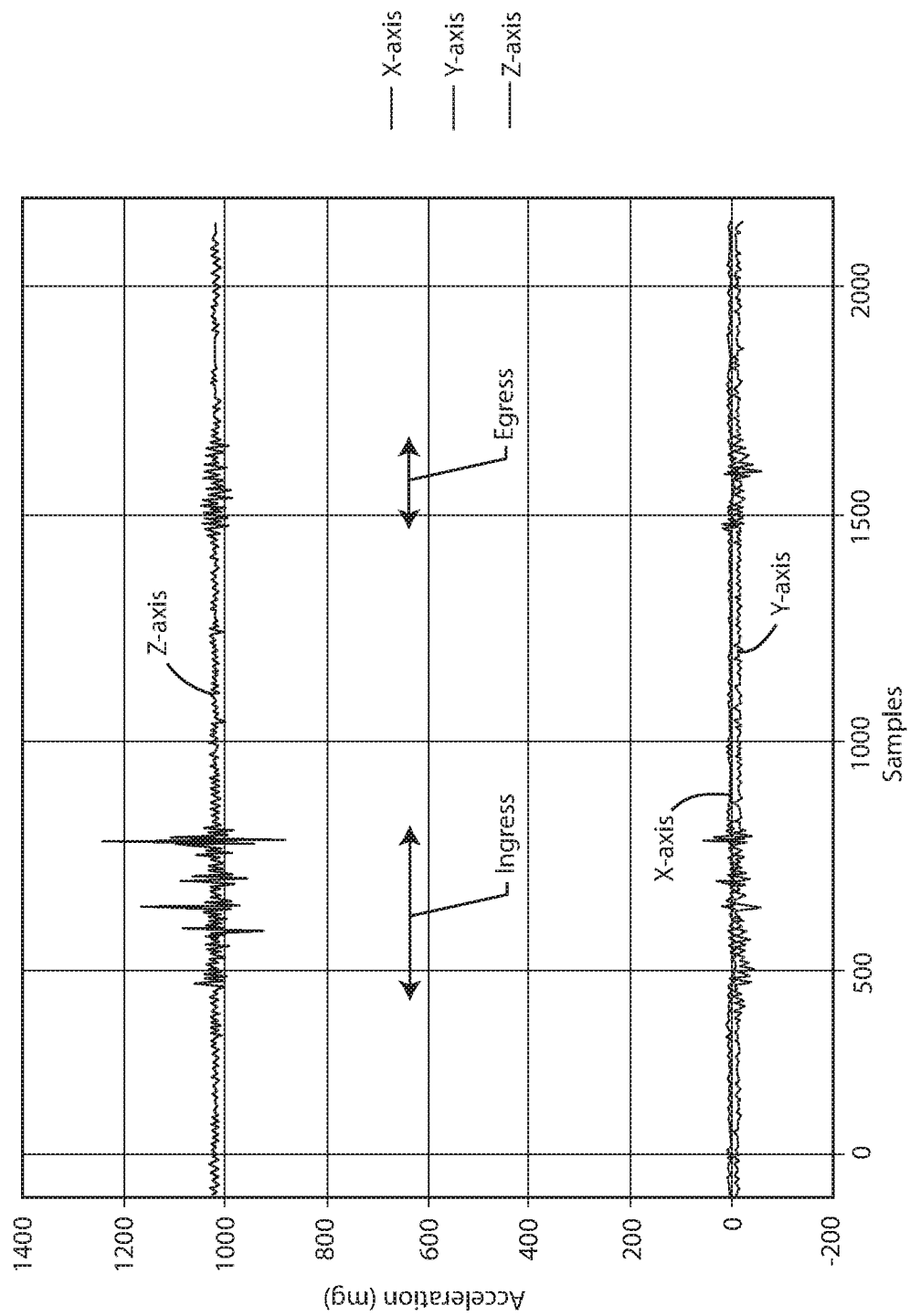
FIG. 7 is another graph of the outputs of one of the accelerometers of FIG. 5 taken while a second person entered the support surface and subsequently exited the support surface.

Controller 58 is also programmed, in at least one embodiment, to characterize the movement of an occupant of support deck 30. Such characterizations include, but are not limited to, sitting up, lying down, exiting, and entering. Controller 58 characterizes these different movements by analyzing the outputs from each of the axes of the different accelerometers. For example, FIGS. 6 and 7 illustrate accelerometer readings taken during the movement of two different individuals who entered, sat up on, and exited a person support apparatus 20. As can be seen from these two graphs, the act of entering the person support apparatus (ingress) generated distinctly different readings in the Z-axis accelerometers than the act of exiting (egress). Further, the egress readings were distinguishable from the act of sitting up while positioned on support deck 30. Controller 58 is programmed, in at least one embodiment, to recognize the types of acceleration patterns, such as those shown in FIGS. 6 and 7, that correspond to entering, exiting, sitting up, and/or lying down on support deck 30.

In one embodiment, person support apparatus 20 uses the recognition of a person entering or exiting support deck 30 from the outputs of accelerometers 62 as a replacement for exit detection system 70. That is, in at least one embodiment, exit detection system 70 is replaced by accelerometers 62. In such a system, an alert is issued when an occupant exits support deck 30, as detected by accelerometers 62 and controller 58 (assuming the exit detection system has been armed). In an alternative system, both accelerometers 62 and force sensors 56 are used for determining whether to issue an exit alert. In this combined embodiment, an exit alert is only generated if the combined outputs of accelerometers and force sensors 56 indicate that an occupant has exited. The manner in which the outputs are combined can be varied in different embodiments.

Controller 58 is also programmed, in at least one embodiment, to utilize the outputs of accelerometers 62 to monitor and record the amount of movement of an occupant of support deck 30. Such monitoring and recording is useful in the treatment and/or prevention of bed sores (decubitis ulcers). Controller 58 repetitively analyzes the outputs from accelerometers 62 to determine if they indicate occupant movement that exceeds an occupant movement threshold. If no such readings are recorded for a first set amount of time, controller 58 provides an alert on display 74 and/or sends a message to an off-board device 76 so that a caregiver is alerted. If this lack of threshold movement continues for a second set amount of time, controller 58 is programmed to send a second message of higher priority to one or more off-board devices 76.

Controller 58 is also adapted to record the detected movements of an occupant and display a history of these movements to a caregiver via display 74, or a display coupled to one or more off-board devices 76. In this manner, a caregiver can review the movement history of a person and determine whether or not sufficient movement has occurred to mitigate the risk of bed sores, or if additional measures should be taken to prevent or treat the sores.

Controller 58 is programmed, in at least one embodiment, to utilize the outputs of height sensor 66 in combination with the outputs from accelerometers 62 and/or force sensors 56 in order to determine whether a potential rollover hazard exists. This determination is made based upon the fact that the higher litter frame 28 is elevated, the higher the center of mass becomes of person support apparatus 20. Further, the higher the center of mass of person support apparatus 20, the less amount of force it takes to roll over, or tip, person support apparatus 20. In at least one embodiment, controller 58 is programmed to utilize the outputs of height sensor 66 and force sensors 56 in order to determine whether a potential rollover hazard exists. In one embodiment, controller 58 makes this determination by estimating how much the center of mass of person support apparatus 20 has changed from an initial unloaded configuration in which litter frame 28 is at its lowest height. The center of mass of person support apparatus 20 when litter frame 28 is unloaded and at its lowest height is calculated at the time of manufacture of person support apparatus 20 and stored in memory 60. Further, the total mass of person support apparatus 20, as well as the mass of litter frame 28 is programmed into memory 60 at the time of manufacture. By measuring how high litter frame 28 is subsequently elevated and how much weight has been added to litter frame 28 by the patient (and/or other items), controller 58 is able to estimate how much the center of mass of person support apparatus 20 (and its load) has changed. If this change exceeds one or more thresholds, controller 58 issues a warning of a potential rollover hazard. The warning is displayed on display 74, in at least one embodiment.

In some embodiments, where controller 58 is programmed to calculate a center of gravity of the load applied to litter frame 28 using force sensors 56, controller 58 utilizes this center of gravity calculation when determining if a rollover hazard exists. Thus, if the load on litter frame 28 is off-center and positioned closer to one of the sides of support deck 30, then the susceptibility of person support apparatus 20 to tipping is increased. The amount of this increase can be estimated by taking into account the total weight on litter frame 28, the height of litter frame 28, and also the calculated position of the center of gravity of the load on litter frame 28. The increased susceptibility to tipping is compared to one or more thresholds, the precise values of which will vary from person support apparatus to person support apparatus, depending upon the particular geometry and construction of the person support apparatus, as would be understood by one skilled in the art.

Controller 58 is also programmed, in at least one embodiment, to utilize the outputs of accelerometers 62 in order to calculate a tilt of the litter 28 with respect to horizontal. More specifically, controller 58 calculates the degree to which the accelerometers 62 have sensed a displacement from vertical along the Z-axis (using frame of reference 78). Controller 58 uses this tilt angle of litter 28 in combination with the outputs from the force sensors 56 and height sensor 66 to perform an additional, or alternative, calculation of whether a potential rollover hazard exists or not. This determination is made based upon the fact that person support apparatus 20 may be more likely to tip when it is positioned on an uneven or sloped floor or other type of surface. In at least one embodiment, controller 58 is programmed to utilize this tilt angle, along with the outputs of height sensor 66 and force sensors 56 in order to determine whether a potential rollover hazard exists. As a result, controller 58 is able to accurately warn of a potential rollover hazard, even in situations where the height of litter 28 and the magnitude and location of its load, by themselves, do not indicate a potential rollover hazard. Controller 58 determines this potential rollover hazard by comparing the measured tilt angle with a threshold angle. The threshold angle may vary for different heights of litter 28, different loads on litter 28, and different locations (e.g. center of gravity) of the load on litter 28.

Still further, in some embodiments, controller 58 determines if person support apparatus 20 will change from a no rollover hazard state to a rollover hazard state through the action of a user raising the height of litter 28. In such an embodiment, controller 58 issues a rollover warning and prevents the user from raising the height of litter 28 (or intentionally tilting litter frame to a Trendelenburg, reverse Trendelenburg, or other sloped orientation) until the conditions causing the potential rollover hazard are addressed (e.g. the load is moved to the center of litter 28 and/or person support apparatus 20 is leveled).

Controller 58 is also programmed, in at least one embodiment, to utilize the outputs of accelerometers 62 to determine whether person support apparatus 20 has experienced an impact of sufficient strength to require replacement, or servicing, of one or more components. When person support apparatus 20 includes force sensors 56, for example, it can become necessary to replace and/or recalibrate the load cells if they are subjected to one or more accelerations exceeding particular thresholds. Other components on person support apparatus 20 may also need to be replaced or serviced when subjected to undue accelerations. Controller 58 is programmed to monitor the outputs of accelerometers 62 and repetitively compare these outputs to the one or more replacement/service thresholds and, if they are exceeded, provide an indication to a user of person support apparatus 20 via display 74, or to provide a remote indication by transmitting a corresponding message to one or more of the off-board devices 76.

In one such embodiment, controller 58 utilizes a known mass (or weight) of litter frame 28 and the measured load on litter frame 28 (as determined from force sensors 56) to determine whether force sensors 56 should be replaced or serviced. Typically, force sensors, such as load cells, have a maximum amount of weight that they are rated to be able to withstand without damage. By knowing the accelerations the load cells were subjected to (via accelerometers 62), along with the total weight they are supporting (e.g. litter frame 28 plus the weight it is supporting, including an occupant, if present), controller 58 estimates how much force was applied to the load cells whenever a major impact is detected by accelerometers 62. If the force exceeds the maximum ratings for one or more of the load cells, controller 58 issues an alert, which may be local (e.g. via display 74) or may be remote (via one or more off-board devices 76).

Controller 58 is also programmed, in at least one embodiment, to utilize the outputs of accelerometers 62 to filter out noise, artifacts, and/or unwanted signal components that are detected by one or more non-accelerometer sensors, such as, for example, force sensors 56. In conventional person support apparatuses 20, it is typically not possible to take an occupant's weight reading using scale system 70 while the occupant is moving or the person support apparatus is otherwise experiencing vibrations or other types of motion. By using accelerometers 62 to detect such vibrations, or other motion, controller 58 is able to filter out those portions of the outputs of force sensors 56 that are due to such vibrations or other motion. This enables person support apparatus 20 to take occupant weight readings during the presence of occupant motion, or other types of motion. Such other types of motion may include vibrations from one or more therapy devices—such as pumps, motors, or devices having other types of moving components—that are used in the care and treatment of a patient associated with person support apparatus 20. One such therapy device is a Deep Vein Thrombosis (DVT) pump that is used with a patient to help treat or prevent DVT. The effects of other types of therapy devices on force sensors 56, or other components, can, of course, also be cancelled out by controller 58 using accelerometers 62.

In some situations, the accelerations sensed by accelerometers 62 while taking a patient weight reading may be too large, or otherwise too difficult, to accurately filter from the outputs of force sensors 56. In those situations, controller 58 is programmed to provide an indication that a valid weight reading was not possible due to excessive movement. This indication may be provided on display 74 or it may be provided on a display coupled to one of the off-board devices 76.

Still further, controller 58 is also programmed, in at least one embodiment, to automatically zero the outputs from force sensors 56 when an occupant is not present on support deck 30. Controller 58 does this by determining when an occupant is absent from support deck 30 (in any of the manners previously described), taking a weight reading and then setting that weight reading equal to a new tare value. When the occupant returns, the scale system uses that new tare value to compute the weight of the occupant. That is, controller 58 subtracts that tare value from the total weight detected by force sensors 56 when the occupant has returned to calculate a weight of the occupant.

It will be understood by those skilled in the art that, although person support apparatus 20 has been described herein as performing a variety of different functions involving accelerometers 62, person support apparatus 20 may be implemented with fewer than all of these functions. That is, controller 58 of person support apparatus 20 can be programmed to perform only a single one of the following functions, or any combination of one or more of the following functions: (1) detecting the presence or absence of an occupant; (2) estimating an impact location; (3) detecting and/or characterizing occupant movement; (4) determining potential damage to one or more components from an impact (5) automatically re-arming the exit detection function; (6) filtering unwanted components out of signals from one or more non-accelerometer sensors; and (7) automatically zeroing the scale system 70.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A person support apparatus comprising:
    a support surface adapted to support a cushioning structure and a person thereon, the support surface including a first section and a second section, the first section being pivotable between a raised orientation and a lowered orientation;
    a litter adapted to support the support surface;
    a first accelerometer positioned below the first section and coupled to the litter such that the first accelerometer does not change orientation when the first section pivots; and
    a controller in communication with the first accelerometer, the controller adapted to process signals from the first accelerometer to detect a presence or absence of the person on the support surface.

2. The person support apparatus of claim 1 wherein the controller is further adapted to automatically execute a task in response to the presence of the person on the support surface.

3. The person support apparatus of claim 1 further including a second accelerometer positioned below the cushioning structure and coupled to at least one of the support surface and the litter, the controller in communication with the second accelerometer and adapted to utilize information regarding the relative position of the second accelerometer with respect to the first accelerometer to estimate a location on the support surface of a disturbance.

4. The person support apparatus of claim 1 further including a plurality of load cells adapted to support said litter, wherein said controller is in communication with the load cells and uses signals from the load cells and the signals from the first accelerometer to detect the presence or absence of the person on the support surface.

5. A person support apparatus comprising:
    a support surface adapted to support a person thereon;
    a litter adapted to support the support surface;
    a plurality of force sensors adapted to detect a load, the load including the support surface and the person when the person is supported on the support surface;
    an accelerometer coupled to at least one of the support surface and the litter; and
    a controller in communication with the accelerometer and the plurality of force sensors, the controller adapted to use an output from the accelerometer to filter an output of at least one of the plurality of force sensors, the controller further adapted to determine if the person has exited the person support apparatus based upon a combination of signals from both the accelerometer and the plurality of force sensors.

6. The person support apparatus of claim 5 wherein the controller is adapted to measure the person's weight based upon outputs from the plurality of force sensors and the controller is further adapted to determine if the measured weight is valid based upon outputs from the accelerometer.

7. The person support apparatus of claim 5 wherein the controller uses a periodic output from the accelerometer to filter the output from the at least one of the plurality of force sensors.

8. The person support apparatus of claim 5 wherein the controller uses a transient output from the accelerometer to filter a contemporaneous portion of the output from the at least one of the plurality of force sensors.

9. The person support apparatus of claim 5 wherein the controller is adapted to measure the person's weight based upon outputs from the plurality of force sensors and the controller is further adapted to use outputs from the accelerometer to determine if the person is present or absent from the person support apparatus.

10. The person support apparatus of claim 5 further comprising:
    a lift subsystem adapted to raise and lower a height of the support surface;
    a height sensor adapted to determine a height of the support surface and report the height to the controller; and
    wherein the controller is adapted to determine an amount of weight exerted on the support surface based on outputs from the plurality of force sensors and the controller is further adapted to determine if a rollover hazard exists based upon the weight exerted on the support surface and the height of the support surface.

11. The person support apparatus of claim 10 wherein the controller is further adapted to determine a center of gravity of the weight exerted on the support surface and use the determined center of gravity when determining if a rollover hazard exists.

12. The person support apparatus of claim 9 wherein the controller is adapted to automatically zero a weight reading from the plurality of force sensors when the person is absent from the person support apparatus.

13. The person support apparatus of claim 9 wherein the controller is adapted to automatically take a tare weight reading from the plurality of force sensors when the person is absent from the person support apparatus.

14. The person support apparatus of claim 13 wherein the controller sends a message to a user interface of the person support apparatus indicating that a tare weight reading has been automatically taken, including a magnitude of the tare weight reading.

15. A person support apparatus comprising:
    a support surface adapted to support a person thereon;
    a litter adapted to support the support surface;
    a plurality of force sensors adapted to detect a load, the load including the support surface and the person when the person is supported on the support surface;

an accelerometer coupled to at least one of the support surface and the litter; and a controller in communication with the accelerometer and the plurality of force sensors, the controller adapted to use outputs from the accelerometer to detect an impact against the person support apparatus, compare a magnitude of the detected impact with a threshold, and, if the threshold is exceeded, to issue a warning indicating potential damage to one or more of the plurality of force sensors.

16. The person support apparatus of claim 15 wherein the controller is adapted to determine a weight of the person based upon outputs from the plurality of force sensors.

17. The person support apparatus of claim 16 wherein the controller is further adapted to indicate that the determined weight of the person may be inaccurate due to the impact.

18. The person support apparatus of claim 15 wherein the person support apparatus is a cot.

19. The person support apparatus of claim 15 wherein the plurality of force sensors are load cells.

20. The person support apparatus of claim 15 further including a second accelerometer in communication with the controller, wherein the controller is adapted to estimate a location of the impact based upon the outputs from the accelerometer and second accelerometer.

* * * * *